United States Patent [19]

Aul et al.

[11] Patent Number: 5,538,718
[45] Date of Patent: *Jul. 23, 1996

[54] COSMETIC STICKS

[75] Inventors: Marta Aul, Buchholz; Manfred Klier, Aumühle; Günter Schneider, Hamburg, all of Germany; Stephan Teichmann, Tairamachi, Japan

[73] Assignee: Beiersdorf Aktiengesellschaft, Hamburg, Germany

[*] Notice: The term of this patent shall not extend beyond the expiration date of Pat. No. 5,466,457.

[21] Appl. No.: 193,148

[22] PCT Filed: Aug. 5, 1992

[86] PCT No.: PCT/DE92/00649

§ 371 Date: Feb. 14, 1994

§ 102(e) Date: Feb. 14, 1994

[87] PCT Pub. No.: WO93/04658

PCT Pub. Date: Mar. 18, 1993

[30] Foreign Application Priority Data

Aug. 29, 1991 [DE] Germany .......................... 41 28 748.7

[51] Int. Cl.$^6$ ...................................................... A61K 7/027
[52] U.S. Cl. ........................ 424/64; 424/401; 424/DIG. 5
[58] Field of Search ......................... 424/64, 401, DIG. 5

[56] References Cited

U.S. PATENT DOCUMENTS

| 5,047,232 | 9/1991 | Kaplan ....................................... 424/59 |
| 5,225,186 | 7/1993 | Castogiovanni et al. ................. 424/64 |

*Primary Examiner*—Jyothsna Venkat
*Attorney, Agent, or Firm*—Sprung Horn Kramer & Woods

[57] ABSTRACT

Compositions for cosmetic sticks, comprising
  (a) beeswax,
  (b) esters of
    (ba) a saturated carboxylic acid having 20–40 carbon atoms and
    (bb) a saturated alcohol having 14–34 carbon atoms,
  (c) if appropriate water, and
  (d) other lipids and/or customary auxiliaries and additives.

8 Claims, No Drawings

COSMETIC STICKS

This application is a 371 of PCT/DE92/00649 filed Aug. 5, 1992.

The present invention relates to cosmetic sticks, in particular lipsticks, preferably lip-care sticks, and to compositions and processes for the production of cosmetic sticks.

The skin of the lips has only an extremely thin horny layer. There are no sweat glands at all on the lips, and only isolated sebaceous glands. The skin of the lips is therefore practically free from oil, and tends to dry out, especially during cold and dry weather. Small cracks can then form in the skin, and the sensitivity of the lips to chemical, physical and microbial actions (for example foodstuffs, sunlight and herpes simplex viruses) increases.

The task of lip-care sticks is to prevent this. These products usually comprise a high content of waxes and fat components which form a covering layer over the lips after application.

Active compounds which promote lip care or lip protection, for example vitamins, moisturising agents, agents giving protection against light, opaque pigments and the like, can additionally be incorporated into the formulations for lip-care sticks.

The corium of the lips contains well-circulated papillae, which extend to just below the surface of the lips. The lips are therefore reddish in colour, and are contrasted in colour to a greater or lesser degree from the remaining skin of the face, depending on the complexion of the person in question. A stylistic means of decorative cosmetics is hence also to match the colour of the lips to the type of person by appropriate cosmetics.

Products of this type are decorative lipsticks, into which the most diverse coloured pigments can be incorporated. These sticks also comprise high contents of waxes and fat components which form a covering lipid layer over the lips after application.

However, the object of this layer at present is not to protect the skin of the lips from drying out. The lipid layer serves here as a base for the incorporated pigments which adheres to the lips; for various reasons, the pigments themselves cannot be applied to the lips without such a base.

It is also possible to combine the properties of the lip-care sticks and decorative lipsticks with one another, i.e. to incorporate lip-care or protective substances into decorative lipsticks.

Technically, almost all lipsticks are anhydrous fatty mixtures of solid or semi-solid waxes and liquid oils, the lipstick base being highly purified paraffin oils and waxes.

According to the ideal profile of requirements, it should be possible to apply lipstick smoothly and without a high frictional resistance. Moreover, even under gentle pressure, a lipstick should give to the lips a fatty film which is not oily, dull or tacky but nevertheless is firmly adhering. This fatty film should then make the lips smooth and supple.

Furthermore, a lipstick must also meet the requirements that it must be break-proof and heat-resistant, and should not lose its oil.

Customary bases of the prior art are (1) liquid oils (for example paraffin oils, castor oil and isopropyl myristate), (2) semi-solid constituents (for example white petroleum jelly and lanolin), (3) solid constituents (for example beeswax, ceresin and microcrystalline waxes or ozokerite) and (4) high-melting waxes (for example carnauba wax and candelilla wax).

Lipsticks of the prior art having a content of paraffins and beeswax are described in "Kosmetik, Entwicklung Herstellung und Anwendung kosmetischer Mittel [Cosmetics, development, preparation and use of cosmetic agents]", page 105, editor: W. Umbach, Georg Thieme Verlag, Stuttgart—New York, 1988.

However, the prior art has a number of disadvantages. These include the fact that water-soluble active compounds are often not sufficiently soluble in fats for them to be incorporated into the cosmetic bases to any appreciable extent. On the other hand, a certain content of water would be entirely desirable, in order to increase the compatibility of the cosmetic stick with the human skin.

A process for the preparation of a cosmetic stick based on a water-in-oil emulsion is known from DBP 2,335,549. According to this teaching, a gel is prepared from a polyhydroxy compound and a nonionic surface-active compound, this gel is mixed with a cosmetic base and a content of water is then emulsified into the mixture.

However, sticks which have the universal requirements imposed on a cosmetic stick cannot be produced by this process.

Another disadvantage is that, up until the present point in time, paraffin oils and waxes were indispensable constituents for lipsticks. Although these are raw materials which are obtainable in high quality, and sticks having usable properties can be formulated with the aid of these substances, the use properties of such cosmetic sticks are limited. Moreover, paraffins are valuable raw materials whose occurrence on the earth is limited. Modern production is progressing in the direction of raw materials which are regenerated, that is to say, for example, vegetable waxes or oils in the field of cosmetics.

However, it was hitherto impossible to design a cosmetic stick based on the known vegetable waxes, fats or oils or chemically modified vegetable waxes, fats or oils. Another object of the present invention was thus to provide a base for cosmetic sticks, in particular lipsticks, which can dispense with mineral oils and instead can be based on vegetable or, if appropriate, animal lipid components or chemically modified variants thereof.

It was surprising and not foreseeable that compositions for cosmetic sticks, which comprise (a) beeswax, (b) esters of
   (ba) a saturated carboxylic acid having 20–40 carbon atoms and
   (bb) a saturated alcohol having 14–34 carbon atoms, (c) if appropriate water, and (d) other lipids and/or customary auxiliaries and additives, would give lipsticks which have all the required properties and which eliminate the disadvantages of the prior art.

In particular, with the compositions according to the invention it is possible to obtain emulsion lipsticks or lip-care sticks and, regardless of whether water is to be incorporated or not, to dispense with the addition of mineral lipid components or paraffins entirely.

The present invention moreover allows emulsion lipsticks which do not have the disadvantages of the prior to be provided.

It is particularly advantageous to select the esters from the group comprising esters of a saturated carboxylic acid having 24–34 carbon atoms and a saturated alcohol having 14–22 carbon atoms.

The esters of a saturated carboxylic acid having 26–32 carbon atoms and a saturated alcohol having 16–20 carbon atoms are particularly advantageous.

The esters (A)–(J) are especially advantageous:

(A) hexacosanyl palmitate (synonym: hexacosanyl hexadecanoate) has the formula

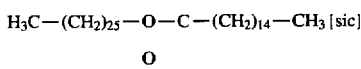

(B) octacosanyl palmitate (synonym: octacosanyl hexadecanoate) has the formula

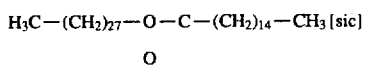

(C) triacontanyl palmitate (synonym: triacontanyl hexadecanoate) has the formula

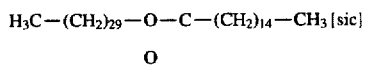

(D) dotriacontanyl palmitate (synonym: dotriacontane hexadecanoate [sic]) has the formula

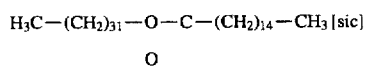

(E) tetratriacontanyl palmitate (synonym: tetratriacontane hexadecanoate [sic]) has the formula

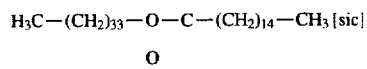

(F) hexacosanyl stearate (synonym: hexacosanyl octadecanoate) has the formula

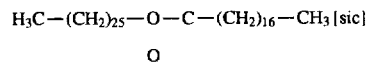

(G) octacosanyl stearate (synonym: octacosanyl octadecanoate) has the formula

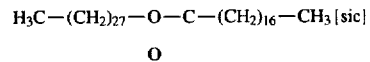

(H) triacontanyl stearate (synonym: triacontanyl octadecanoate) has the formula

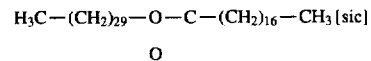

(I) dotriacontanyl stearate (synonym: dotriacontanyl octahexadecanoate [sic]) has the formula

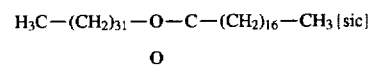

(J) tetratriacontanyl stearate (synonym: tetratriacontanyl octadecanoate) has the formula

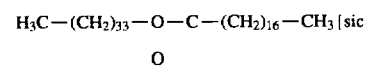

The preferred ester is octacosanyl stearate.

The esters were synthesised and provided by Koster Keunen Holland B. V.

Because of their preparation, the esters may possibly contain certain harmless by-products and unreacted starting substances. It is advantageous to employ commercial products, the ester content of which comprises at least 80% by weight, based on the total weight of the product.

Beeswax (synonyms are: cera flava (yellowish) and cera alba (white), CTFA: beeswax) consists mainly of myricyl palmitate, cerotic acid, melissic acid, higher alcohols and hydrocarbons. Recent studies suggest that beeswaxes consist of a homologous series of chiefly hexadecanoate alkyl esters between $C_{35}$ and $C_{54}$ ("Lexikon der Hilfsstoffe für Pharmazie, Kosmetik und angrenzende Gebiete [Dictionary of auxiliaries for pharmacy, cosmetics and related fields]", H. P. Fiedler, 3rd edition, 1989, Editio Cantor Aulendorf, and the sources and cross-references quoted therein under the keyword "beeswax").

From ancient times, beeswax has been an important cosmetic constituent, in particular for creams and ointment formulations, but also for cosmetic sticks. A lipstick of the prior art comprises 4.0% by weight of beeswax.

Beeswax contents which are too high have hitherto always meant that cosmetic sticks were lustreless and granular. The stability of such sticks also constantly left something to be desired. It was always a considerable disadvantage that cosmetic sticks based on beeswax were cosmetically inelegant.

Needless to say, a certain amount of beeswax, as is known, imparts strength to lipsticks and causes the lipstick composition to adhere firmly to the lips ("Kosmetik, Entwicklung, Herstellung und Anwendung kosmetischer Mittel ["Cosmetics, development, preparation and use of cosmetic agents]", page 104 and passim, W. Umbach (editor), 1988, Georg Thieme Verlag, Stuttgart).

Nevertheless, beeswax, certainly from the above considerations, is not an obligatory constituent of cosmetic sticks.

The cosmetic sticks according to the invention advantageously comprise 0.5–50% by weight of beeswax, 0.5–50% by weight of an ester of a saturated carboxylic acid having 20–40 carbon atoms and a saturated alcohol having 14–34 carbon atoms and 0.1–20% by weight of water, in particular 2.0–20% by weight of beeswax, 2.0–25% by weight of an ester of a saturated carboxylic acid having 20–40 carbon atoms and a saturated alcohol having 14–34 carbon atoms and 1.0–10% by weight of water, preferably 3.0–10% by weight of beeswax, 5.0–20% by weight of an ester of a saturated carboxylic acid having 20–40 carbon atoms and a saturated alcohol having 14–34 carbon atoms and 1.0–5% by weight of water, especially preferably 4.0–6.0% by weight of beeswax, 15.0–18.0% by weight of an ester of a saturated carboxylic acid having 20–40 carbon atoms and a saturated alcohol having 14–34 carbon atoms and 2.0–3.0% by weight of water.

It is preferable to choose a ratio of beeswax and one or more esters of a saturated carboxylic acid having 20 to 40 carbon atoms and a saturated alcohol having 14–34 carbon atoms, in particular the esters (A)–(J), particularly preferably octacosanyl stearate, in a ratio [sic] of about 1:1 to about 1:5, in particular about 1:3.

The compositions according to the invention which are used as bases for emulsion lipsticks thus comprise a certain amount of water. It is indeed possible to dispense with an emulsifier, since beeswax itself has emulsifier properties.

However, it is advantageous and preferable to incorporate an emulsifier, in particular a water-in-oil emulsifier (W/O emulsifier).

The polyglycerol fatty acid esters have, surprisingly, proved to be particularly preferred W/O emulsifiers, which lead to surprisingly stable cosmetic sticks which are particularly skin-friendly, and moreover give recipes which are particularly elegant from the cosmetic point of view. Polyglyceryl 3-diisostearate (synonym: triglyceryl diisostearate) is particularly advantageous.

The polyglycerol esters which are advantageous according to the invention and their occurrence, properties and use in cosmetics are listed and discussed in "Lexikon der Hilfsstoffe für Pharmazie, Kosmetik und angrenzende Gebiete [Dictionary of auxiliaries for pharmacy, cosmetics and related fields]", H. P. Fiedler, 3rd edition, 1989, Editio Cantor Aulendorf, and the sources and cross-references quoted therein under the keywords "polyglycerin esters", "polyglycerol esters", "polyglyceryl 3 diisostearates", "triglycerol" and "triglyceryl diisostearate" and the like. The polyglycerol esters described therein are particularly suitable for the present invention.

The invention thus relates to cosmetic sticks which, in addition to being characterised by a content of beeswax, octacosanyl stearate and water, are characterised in that they comprise one or more emulsifiers from the group comprising polyglycerol fatty acid esters, in particular polyglyceryl 3-diisostearate.

The emulsifiers can advantageously be incorporated into the compositions according to the invention in contents of 0.05–10.0% by weight, in particular in contents of 1.00–8.00% by weight, particularly preferably 2.00–4.00% by weight.

The customary constituents of cosmetic sticks can advantageously be incorporated into the formulations according to the invention, that is to say waxes, in particular vegetable and/or animal waxes or chemically modified derivatives thereof, in particular carnauba wax, candelilla wax and the like, hydrocarbons, fats and oils for the base substance, and the customary auxiliaries and additives, such as perfume oils, preservatives, coloured pigments, agents giving protection against light and stabilisers.

It is additionally possible to incorporate lip-care active compounds, which are not limited to the fat-soluble active compounds, as previously, but can also be chosen from the group comprising water-soluble active compounds, for example vitamins and the like.

It is particularly advantageous to choose the remainder of the stick composition to make up 100% by weight from the group comprising the following substances:

glycerol tricarboxylic acid esters (synonym: triglycerides), Guerbet alcohols, myristyl myristate, jojoba oil and related substances. In particular, other liquid fat components can advantageously be incorporated into the compositions according to the invention, these including, for example, fractionated coconut oils.

Additional auxiliaries and additives and active compounds, in particular lip-care active compounds, which are not limited to the fat-soluble active compounds, as previously, but can also be chosen from the group comprising water-soluble active compounds, for example vitamins and the like, can also advantageously be incorporated here.

The invention thus also relates to compositions for cosmetic sticks, comprising (a) beeswax, (b) octacosanyl stearate and (c) water, and substances chosen from the group comprising (d) glycerol tricarboxylic acid esters, (e) Guerbet alcohols, (f) myristyl myristate, (g) jojoba oil and (h) fractionated coconut oils, and if appropriate additionally substances chosen from the group comprising waxes, hydrocarbons, fats, oils, other auxiliaries and additives, such as perfume oils, preservatives, coloured pigments, agents giving protection against light and stabilisers, and fat-soluble and/or water-soluble active compounds.

However, for the abovementioned reasons, it is advantageous to dispense with hydrocarbons entirely. Nevertheless, the compositions according to the invention, even together with hydrocarbons, give extremely elegant cosmetic sticks having advantageous properties.

The glycerol triesters can advantageously be chosen from the group comprising the so-called Neobee oils, and fats. On the prior art of glycerol triesters and their occurrence, properties and use in cosmetics, see "Lexikon der Hilfsstoffe für Pharmazie, Kosmetik und angrenzende Gebiete [Dictionary of auxiliaries for pharmacy, cosmetics and related fields]", H. P. Fiedler, 3rd edition, 1989, Editio Cantor Aulendorf, and the sources and cross-references quoted therein under the keyword "triglycerides". The triglycerides described therein are particularly suitable for the present invention.

Guerbet alcohols are understood as meaning branched-chain alcohols of the general formula

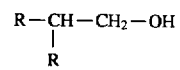

In this formula, R preferably represents $C_6$ to $C_{12}$ hydrocarbon radicals (on the prior art of the preparation, properties and use of Guerbet alcohols: "Lexikon der Hilfsstoffe für Pharmazie, Kosmetik und angrenzende Gebiete [Dictionary of auxiliaries for pharmacy, cosmetics and related fields]", H. P. Fiedler, 3rd edition, 1989, Editio Cantor Aulendorf, and the sources and cross-references quoted therein under the keyword "Guerbet alcohols").

Although it is conceivable, and may be advantageous, for sticks according to the present invention also to be designed for uses other then as lipsticks, for example as deodorant sticks, comparatively low consumer acceptance is to be expected in the fields of use in question, since the compositions according to the invention usually have a slightly greasy effect. The latter is also entirely desirable and very pleasant in the case of a lipstick.

However, it is expected of a deodorant stick, at any rate according to the judgement of the central European consumer spectrum, precisely that it is not greasy.

The cosmetic sticks according to the invention can advantageously be produced by a process which is characterised in that (1) beeswax and octacosanyl stearate, and if appropriate one or more emulsifiers chosen from the group comprising W/O emulsifiers, in particular polyglycerol fatty acid esters, particularly advantageously: polyglyceryl 3-diisostearate, and fat components chosen from the group comprising glycerol tricarboxylic acid esters, Guerbet alcohols, myristyl myristate, jojoba oil and/or related substances and fractionated coconut oils, are melted, and if appropriate are subjected to steps (2) and (3), that is to say (2) water is added continuously until the desired water content of the cosmetic stick is reached, (3) the resulting mixture is stirred during the addition of water, (4) and the uniformly stirred mixture is then introduced into casting moulds and is allowed to cool slowly.

The present invention is to be described in the following examples, but without it being intended to limit the present invention. Rather, the expert has available an abundance of modifications, slight changes and the like which he can make on the basis of his expert knowledge without having to depart from the basis of the present invention. The individual starting substances are chosen analogously to CTFA nomenclature, apart from those substances for which a simple chemical name exists (for example: water).

EXAMPLE 1

|  | % by weight |
|---|---|
| Caprylic/capric triglycerides | 25 |
| Octyldodecanol | 25 |
| Caprylic/capric diglyceryl succinates | 5 |
| Jojoba oil | 5 |
| Myristyl myristate | 10 |
| Octacosanyl stearate | 20 |
| Beeswax, white | 9 |
| Octyl methoxycinnamate | 1 |

EXAMPLE 2

|  | % by weight |
|---|---|
| Octyldodecanol | 45 |
| Caprylic/capric diglyceryl succinates | 10 |
| Squalane | 7 |
| Jojoba oil | 3 |
| Myristyl myristate | 8 |
| Carnauba wax | 2 |
| Octacosanyl palmitate | 11 |
| Octacosanyl stearate | 4 |
| Beeswax, white | 10 |

EXAMPLE 3

|  | % by weight |
|---|---|
| Cetyl palmitate | 8 |
| Squalane | 15 |
| Wheatgerm oil | 5 |
| Propylene glycol dicaprylate/caproate | 10 |
| Caprylic/capric triglycerides | 10 |
| Octyldodecanol | 20 |
| Polyisobutene | 2 |
| Cyclomethicone | 10 |
| Hexacosanyl palmitate | 10 |

EXAMPLE 4

|  | % by weight |
|---|---|
| Beeswax, white | 26 |
| Caprylic/capric diglyceryl succinates | 15 |
| Propylene glycol Dicaprylates/dicaprates | 7 |
| Caprylic/capric triglycerides | 24 |
| Squalane | 10 |
| Shea butter | 7 |

|  | % by weight |
|---|---|
| Octacosanyl stearate | 6 |
| Octyl methoxycinnamate | 5 |

EXAMPLE 5

|  | % by weight |
|---|---|
| Caprylic/capric triglycerides | 14 |
| Octyldodecanol | 20 |
| Jojoba oil | 10 |
| Myristyl myristate | 10 |
| Octacosanyl stearate | 20 |
| Cetyl palmitate | 2 |
| Beeswax, white | 8 |
| Polyglyceryl 3-diisostearate | 4 |
| Glycine | 1 |
| $ZnSO_4.H_2O$ | 1 |
| Water (the pH is adjusted to 6–7 with NAOH) | 10 |

EXAMPLE 6

|  | % by weight |
|---|---|
| Caprylic/capric triglycerides | 20 |
| Octyldodecanol | 15 |
| Cetearyl alcohol | 5 |
| Shea butter | 10 |
| Jojoba oil | 8 |
| Polyglyceryl 3-diisostearate | 2 |
| Polyisobutene | 2 |
| Octacosanyl stearate | 10 |
| Cetyl palmitate | 5 |
| Beeswax, white | 10 |
| Glycerol | 3 |
| Wheatgerm oil | 2 |
| Triacontanyl palmitate | 5 |
| Water | 3 |

EXAMPLE 7

|  | % by weight |
|---|---|
| Octyldodecanol | 42 |
| Caprylic/capric diglyceryl succinates | 5 |
| Squalane | 5 |
| Jojoba oil | 5 |
| Myristyl myristate | 8 |
| Octacosanyl stearate | 20 |
| Beeswax, white | 10 |
| Polyglyceryl 3-diisostearate | 2 |
| Water | 3 |

EXAMPLE 8

|  | % by weight |
|---|---|
| Caprylic/capric triglycerides | 25 |
| Octyldodecanol | 11 |
| Caprylic/capric diglyceryl succinates | 12.5 |
| Propylene glycol dicaprylate/dicaprate | 7 |
| Beeswax, white | 26 |
| Polyglyceryl 3-oleate | 3.5 |
| Octacosanyl palmitate | 5 |
| Water | 10 |

EXAMPLE 9

|  | % by weight |
| --- | --- |
| Jojoba oil | 4 |
| Myristyl myristate | 7 |
| Polyglyceryl 3-oleate | 4 |
| Glyceryl lanolate | 1.5 |
| Wool wax alcohol | 1 |
| Octacosanyl stearate | 5 |
| Ceresin | 15 |
| Caprylic/capric diglyceryl succinates | 12.5 |
| Propylene glycol dicaprylate/dicaproate | 7 |
| Caprylic capric triglycerides | 2.5 |
| Octyldodecanol | 33 |
| Cetearyl alcohol | 0.5 |
| Tocopheryl acetate | 0.1 |
| Water | 4.9 |

EXAMPLE 2

[sic]

The cosmetic sticks according to Examples 1–9 were evaluated by subjective and objective rating criteria.

Subjective rating criteria were the feeling on application (blunt, supple, greasy, oily, tacky) and the visual impression (matt, shiny). In all cases, the cosmetic sticks according to the invention were distinguished by a superior feel on application and an excellent visual impression.

The objective rating criteria were stability to fracture, abrasion of the composition, penetration.

In comparison with compositions of the prior art, the compositions according to the invention had an improved stability to fracture.

The abrasion of the composition is easy to determine by drawing the stick along a substrate with a defined pressing force. Sticks having a low abrasion of the composition are perceived to be dry, and sticks having a high abrasion of the composition are perceived to be oily.

In comparison with compositions of the prior art, the compositions according to the invention had an improved abrasion of the composition. The composition abrasion values are in the range associated with a very pleasant feeling during use.

The penetration is to be determined by measuring the penetration depth of a pointed needle into the lipstick composition. Stick compositions into which the needle scarcely penetrates are perceived to be hard, and those into which the needle penetrates very easily is [sic] also slightly unpleasant, because they are perceived to be too soft.

In comparison with compositions of the prior art, the compositions according to the invention had an improved penetration. The penetration values are in the range associated with a very pleasant feeling during use.

We claim:

1. A cosmetic stick by weight consisting of
   a) 0.5 to 50% of beeswax,
   b) 0.5 to 50% of at least one ester selected from the group consisting of hexacosanyl palmitate, octacosanyl palmitate, triacontanyl palmitate, dotriacontanyl palmitate, tetratriacontanyl palmitate, hexacosanyl stearate, octacosanyl stearate, triacontanyl stearate, dotriacontanyl stearate and tetratriacontanyl stearate,
   c) 0.1 to 20% of water, and
   d) 0.005 to 10% of polyglyceryl 3-diisostearate,
   and further containing at least one fatty component selected from the group consisting of
   e) a Guerbet alcohol,
   f) myristyl myristate,
   g) jojoba oil, and
   h) a fractionated coconut oil, as well as further containing at least one member selected from the group consisting of a wax, hydrocarbon fat, oil, perfume oil, preservative, colored pigment, agent giving protection against light, a stabilizer, and a fat-soluble or water-soluble active compound.

2. A cosmetic stick according to claim 1, by weight consisting of
   2.0–20% (a)
   2.0–25% (b)
   and
   1.0–10% (c).

3. A cosmetic stick according to claim 1, by weight consisting of
   3.0–10% (a)
   5.0–20% (b)
   and
   1.0–5% (c).

4. A cosmetic stick according to claim 1, by weight consisting of
   4.0–6.0% (a)
   15.0–18.0% (b)
   and
   2.0–3.0% (c).

5. A cosmetic stick according to claim 1, wherein (b) is present in from 1 to 5 times the weight of (a).

6. A cosmetic stick according to claim 1, wherein (b) is present in from 1 to 3 times the weight of (a).

7. A lipstick according to claim 1.

8. A method of producing a cosmetic stick according to claim 1, which comprises mixing and melting together (a), (b) and (d), adding water (c) thereto with stirring, pouring the mixture into a mold, and permitting it there to harden into the stick.

* * * * *